United States Patent [19]

Gross et al.

[11] Patent Number: 4,972,935

[45] Date of Patent: * Nov. 27, 1990

[54] APPARATUS FOR FIXING THE POSITION OF TEST ZONES OF A TEST STRIP AND FOR REVERSING THE LATTER

[75] Inventors: Jürgen Gross, Hofheim am Taunus; Rüdiger Simonek, Hans D. Sanger, both of Frankfurt am Main, all of Fed. Rep. of Germany

[73] Assignee: Hoechst Aktiengesellschaft, Frankfurt am Main, Fed. Rep. of Germany

[*] Notice: The portion of the term of this patent subsequent to Oct. 18, 2005 has been disclaimed.

[21] Appl. No.: 78,662

[22] Filed: Jul. 28, 1987

[30] Foreign Application Priority Data

Jul. 30, 1986 [DE] Fed. Rep. of Germany ....... 3625704

[51] Int. Cl.$^5$ .............................................. B65G 47/24
[52] U.S. Cl. ..................................... 198/395; 198/399
[58] Field of Search ..................... 198/395, 399, 463.6, 198/689.1, 404; 221/158

[56] References Cited

U.S. PATENT DOCUMENTS 3,724,648  4/1973  Schaller ............................ 198/463.6
4,777,907  10/1988  Sanger ................................... 198/399

FOREIGN PATENT DOCUMENTS 56-413  5/1981  Japan .................................... 198/395

Primary Examiner—Joseph E. Valenza
Attorney, Agent, or Firm—Finnegan, Henderson, Farabow, Garrett, and Dunner

[57] ABSTRACT

In the apparatus for fixing the position of the test zones of a test strip and for reversing the latter, a guide (8) opens into a reversing device (1, 1a) for the test strips (2). Between the guide and the reversing device is arranged a closing means (9) for the guide, which is connected to a holding device (10) via a lever (5). The holding device (10) projects into the guide and is mounted rotatably in synchronism with the closing means (9). It is also equipped with a drive device (7). The reversing device has a moveable stop (4, 4a) which is driven by a position-detection means (3) arranged in the guide (8).

3 Claims, 1 Drawing Sheet

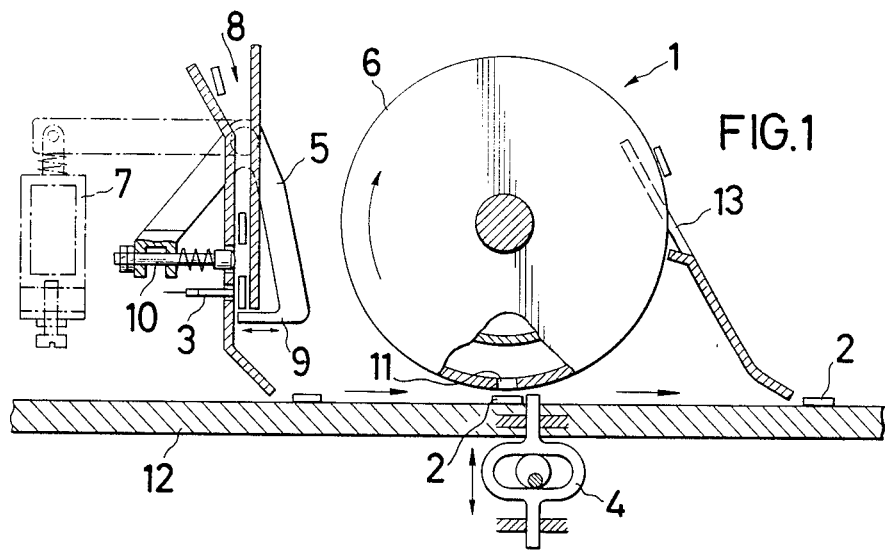
FIG.1
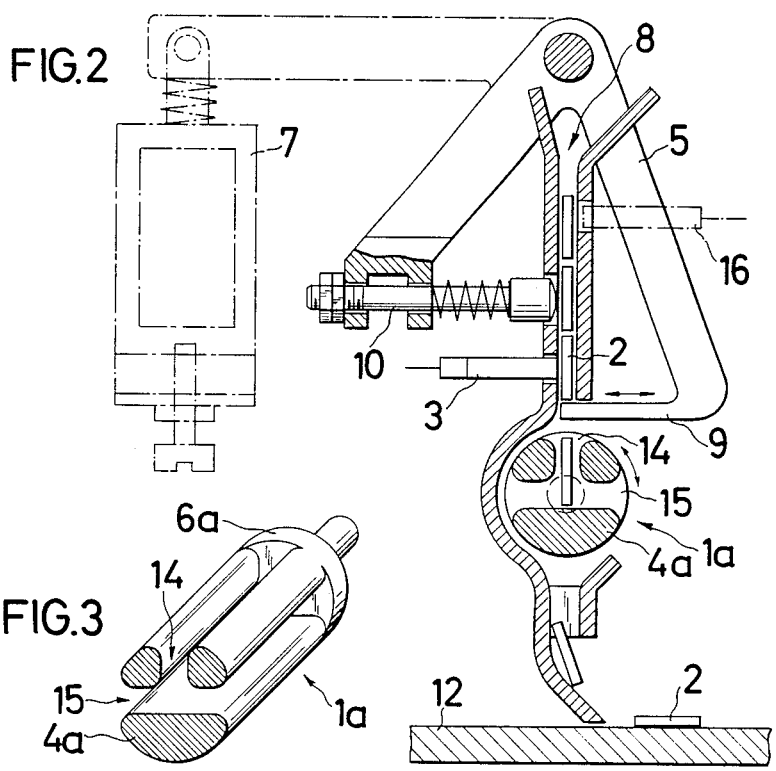
FIG.2
FIG.3

APPARATUS FOR FIXING THE POSITION OF TEST ZONES OF A TEST STRIP AND FOR REVERSING THE LATTER

DESCRIPTION

The invention relates to an apparatus for fixing the position of the test zones of a test strip and for reversing the latter, such test strips being used, for example, for medical tests, especially for analyzing urine. It is part of a line serving for the automatic feeding, sorting, moistening and insertion of test strips in an analyzer, for example a multi-channel photometer.

For generally known urine diagnostics, so-called multiple test strips for determining bilirubin, urobilinogen, ketone bodies, ascorbic acid, glucose, protein, nitrite, pH and blood are available. Test strips of this type contain several test zones, on which the reagents belonging to the particular test are arranged as indicators. The test strips are moistened with urine by hand and are subsequently introduced into the analyzer. This work is to be automated. Among other things, an apparatus for fixing the position of the test zones and, if appropriate, reversing the test strips, so that the test zones of all the strips face upwards, is necessary for this purpose.

The invention achieves the object by a guide opening into a reversing device for the test strips, there being arranged between the guide and reversing device a closing means for the guide, the said closing means being connected via a lever to a holding device for the test strips which projects into the guide, is mounted rotatably in synchronism with the closing means and is equipped with a drive device, and the reversing device having a moveable stop which is driven by a position-detection means arranged in the guide and which causes the test strips.

The reversing device can comprise an evacuable rotatably mounted hollow roller which is arranged at a distance above a transport device for the test strips and with this forms a gap and which, on its peripheral surface, has a leakage orifice, via which the test strip is sucked up and taken up by the roller when the stop, arranged in the gap between the roller and transport device, has stopped the test strip. However, the reversing device can also comprise a roller which has a T-shaped slot parallel to its axis of rotation, and the part of the roller located opposite the crosspiece of the T-contour is designed as a stop. A monitoring device for the test-strip supply can be arranged in the guide.

The invention is explained in detail below with reference to drawings which illustrate only one possible embodiment.

FIG. 1 shows a side view of the apparatus in section,

FIG. 2 shows an alternative form of the apparatus, likewise in a side view and in section, and FIG. 3 shows the roller according to FIG. 2 in an isometric representation, partially in section.

The apparatus has a guide (8) which opens into a reversing device (1), (1a) for the test strips (2). Between the guide (8) and the reversing device (1), (1a) is arranged a closing means (9) for the guide. The closing means (9) is connected via a lever (5) to a holding device (10), for example a spring-loaded plunger for the test strips (2). The holding device (10) projects into the guide (8) and is mounted rotatably in synchronism with the closing means. When the closing means (9) allows the test strip to pass out of the guide (8), the following test strip is retained in the guide by the holding device (10), until the guide is closed again. The holding device and closing means are equipped with a drive device (7). The reversing device (1), (1a) has a moveable stop (4), (4a) which is driven by means of the prepared pulses from a position-detection means (3), for example a reflex-light barrier. The position of the test zone on the test strip is fixed by the position detection means (3). If it points in the wrong direction, the stop prevents the test strip from being transported further to the analyzer (not shown). The test strip is reversed. Reversal can be carried out, according to FIG. 1, by means of a hollow roller (6) which is evacuable and which has a leakage orifice (11). When the test strip is stopped by the stop (4), it is sucked up by the vacuum via the leakage orifice, held on the roller periphery and reversed in the direction of the arrow as a result of the rotation of the roller. The test strip is taken off the roller by means of the stripper (13).

According to FIG. 2, reversal is carried out by means of a roller (6a) which is provided with a slot of T-shaped cross-section parallel to its axis of rotation. The orifice (15) is intended as a passage orifice in the roller (6a), whilst the crosspiece (14) of the T-contour ends at the stop (4a). When the position-detection means (3) signals the correct position of the test strip, the test strip can pass through the roller (6a) without obstruction. Otherwise, it is stopped by the stop (4a) and reversed through 180° as a result of the rotation of the roller (6a). In order to monitor the test-strip supply in the guide, the latter can be equipped with a monitoring device (16).

We claim:

1. An apparatus for fixing the positions of test zones formed on a test strip and for selectively reversing the orientation of the test strip, comprising:

means for guiding the test strips onto a transport device, said transport device configured with a conveying surface for conveying the test strips, and said guide means defining a channel through which the test strips pass;

reversing means for selectively reversing the orientation of said test strips relative to the conveying surface of said transport device, said reversing means comprising:

an evacuable, rotatably mounted hollow roller having a peripheral surface disposed a predetermined distance above said conveying surface and having a leakage orifice formed in said peripheral surface, and means for evacuating the interior of said hollow roller;

a movable stop and means for selectively inserting and withdrawing said stop through a gap in said conveying surface to selectively stop a test strip resting on said conveying surface immediately below said leakage orifice; and position detecting means, disposed adjacent said channel formed by said guide means, for detecting the orientation of test strips in said channel and for selectively operating said evacuation means, said movable stop, and said roller such that when the orientation of the test strip is to be reversed on the conveying surface the test strip is drawn onto said leakage orifice and the roller is rotated to turn the test strip 180° relative to the conveying surface, and when the orientation of the test strip on the conveying surface is correct the movable stop is withdrawn and the test strip continues on the transport device uninterrupted by said roller;

closing means for selectively blocking and opening said channel defined by said guide means, said closing means being connected via a lever arm to a holding device which removably projects into said channel; and drive means for rotating said lever arm to synchronously block said channel with said closing means and remove said holding device from said channel, and vice-versa, thereby feeding said test strips one by one through the guide means and onto the transport device.

2. The apparatus of claim 1, including monitoring means, disposed adjacent the channel defined by said guide means, for monitoring the number of test strips in said guide means.

3. An apparatus for reversing the orientation of a test strip relative to a conveying surface, comprising:

a conveying surface for receiving and conveying the test strip;

means for guiding the test strip onto said conveying surface;

means for stopping the test strip at a predetermined location on said conveying surface;

an evacuable, rotatably mounted hollow roller having a peripheral surface disposed above said conveying surface, said peripheral surface having a leakage orifice formed therein, said orifice being disposed adjacent said predetermined location on said conveying surface;

means for evacuating the interior of said roller to suck a test strip which has been stopped at said predetermined location toward the leakage orifice and onto the peripheral surface of said roller, subsequent rotation of said roller thereby reversing the orientation of the test strip on the conveying surface; and means for removing the test strip from the peripheral surface of said roller and returning the test strip to the conveying surface in reversed orientation.

* * * * *